US007850737B2

(12) United States Patent
Morrey (10) Patent No.: US 7,850,737 B2
(45) Date of Patent: Dec. 14, 2010

(54) PROSTHETIC ELBOW REPLACEMENT

(75) Inventor: Bernard F. Morrey, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 163 days.

(21) Appl. No.: 12/306,407

(22) PCT Filed: Jun. 26, 2007

(86) PCT No.: PCT/US2007/014766

§ 371 (c)(1),
(2), (4) Date: Dec. 23, 2008

(87) PCT Pub. No.: WO2008/002545

PCT Pub. Date: Jan. 3, 2008

(65) Prior Publication Data

US 2009/0312840 A1 Dec. 17, 2009

Related U.S. Application Data

(60) Provisional application No. 60/816,947, filed on Jun. 28, 2006.

(51) Int. Cl.
*A61F 2/38* (2006.01)
(52) U.S. Cl. .................. 623/20.12; 623/20.11
(58) Field of Classification Search ... 623/20.11–20.15, 623/19.11, 19.12, 19.13, 19.14, 18.11, 17.14, 623/20.22, 20.24, 20.25, 20.26, 21.11, 21.12, 623/21.13
See application file for complete search history.

(56) References Cited

U.S. PATENT DOCUMENTS

| 2,696,817 | A |   | 12/1954 | Prevo |   |
|---|---|---|---|---|---|
| 3,708,805 | A | * | 1/1973 | Scales et al. | 623/20.12 |
| 3,772,709 | A |   | 11/1973 | Swanson |   |
| 3,816,854 | A | * | 6/1974 | Schlein | 623/20.12 |
| 3,824,630 | A | * | 7/1974 | Johnston | 623/20.22 |
| 3,852,831 | A | * | 12/1974 | Dee | 623/20.11 |
| 3,868,730 | A |   | 3/1975 | Kaufer et al. |   |

(Continued)

OTHER PUBLICATIONS

PCT/US07/14766 International Search Report mailed Apr. 17, 2008.

*Primary Examiner*—Alvin J. Stewart
(74) *Attorney, Agent, or Firm*—Quarles & Brady, LLP (57) ABSTRACT

A prosthetic elbow replacement includes a humeral component having a stem dimensioned to fit within a medullary canal of the humerus and having a yoke connected to the stem wherein the yoke terminates in spaced apart arms. A pivot pin is mounted between the arms for rotational movement with respect to the humeral component. The pivot pin has a transverse throughhole. There is an ulnar component having an ulnar stem including a distal end dimensioned to fit within a medullary canal of the ulna and an opposite proximal end dimensioned to fit within a first end opening of the throughhole. The ulnar component has a mounting cap dimensioned to fit within a second end opening of the throughhole. A fastener connects the ulnar stem and the mounting cap such the proximal end of the ulnar stem is positioned within the first end opening of the throughhole and the mounting cap is positioned within the second end opening of the throughhole. The pivot pin rotates to allow for flexion of the prosthetic elbow replacement, and also allows for axial rotation of the ulna component in the humeral component.

20 Claims, 3 Drawing Sheets

U.S. PATENT DOCUMENTS

| | | | | |
|---|---|---|---|---|
| 3,909,854 A * | 10/1975 | Martinez | | 623/20.26 |
| 3,939,496 A * | 2/1976 | Ling et al. | | 623/20.12 |
| 3,990,117 A * | 11/1976 | Pritchard et al. | | 623/20.12 |
| 4,001,896 A * | 1/1977 | Arkangel | | 623/20.24 |
| 4,008,495 A | 2/1977 | Cavendish et al. | | |
| 4,079,469 A * | 3/1978 | Wadsworth | | 623/20.12 |
| 4,131,956 A | 1/1979 | Treace | | |
| 4,131,957 A * | 1/1979 | Bokros | | 623/23.4 |
| 4,136,405 A * | 1/1979 | Pastrick et al. | | 623/20.25 |
| 4,194,250 A * | 3/1980 | Walker | | 623/23.39 |
| 4,242,758 A * | 1/1981 | Amis et al. | | 623/20.11 |
| 4,262,368 A * | 4/1981 | Lacey | | 623/20.25 |
| 4,280,231 A * | 7/1981 | Swanson | | 623/20.11 |
| 4,293,963 A * | 10/1981 | Gold et al. | | 623/20.11 |
| 4,301,553 A * | 11/1981 | Noiles | | 623/20.25 |
| 4,383,337 A * | 5/1983 | Volz et al. | | 623/20.12 |
| 4,538,306 A * | 9/1985 | Dorre et al. | | 623/20.13 |
| 4,759,768 A * | 7/1988 | Hermann et al. | | 623/18.11 |
| 4,822,364 A * | 4/1989 | Inglis et al. | | 623/20.12 |
| 5,061,271 A | 10/1991 | Van Zile | | |
| 5,314,484 A * | 5/1994 | Huene | | 623/20.12 |
| 5,370,701 A * | 12/1994 | Finn | | 623/20.25 |
| 5,376,121 A * | 12/1994 | Huene et al. | | 623/20.12 |
| 5,411,555 A * | 5/1995 | Nieder | | 623/20.26 |
| 5,702,471 A * | 12/1997 | Grundei et al. | | 623/21.16 |
| 5,723,015 A | 3/1998 | Risung et al. | | |
| 5,782,923 A * | 7/1998 | Engelbrecht et al. | | 623/20.13 |
| 5,954,770 A * | 9/1999 | Schmotzer et al. | | 623/20.24 |
| 5,997,543 A * | 12/1999 | Truscott | | 606/86 R |
| 6,019,794 A * | 2/2000 | Walker | | 623/20.22 |
| 6,027,534 A | 2/2000 | Wack et al. | | |
| 6,143,034 A * | 11/2000 | Burrows | | 623/20.29 |
| 6,290,725 B1 * | 9/2001 | Weiss et al. | | 623/20.12 |
| 6,379,387 B1 | 4/2002 | Tornier | | |
| 6,699,290 B1 * | 3/2004 | Wack et al. | | 623/20.12 |
| 6,716,248 B2 | 4/2004 | Huene | | |
| 6,767,368 B2 * | 7/2004 | Tornier | | 623/20.12 |
| 6,773,461 B2 * | 8/2004 | Meyers et al. | | 623/20.24 |
| 6,890,357 B2 | 5/2005 | Tornier | | |
| 6,997,957 B2 | 2/2006 | Huene | | |
| 7,247,170 B2 * | 7/2007 | Graham et al. | | 623/20.13 |
| 7,572,292 B2 * | 8/2009 | Crabtree et al. | | 623/20.24 |
| 7,604,666 B2 * | 10/2009 | Berelsman et al. | | 623/20.12 |
| 7,608,110 B2 * | 10/2009 | O'Driscoll et al. | | 623/20.11 |
| 7,625,406 B2 * | 12/2009 | Berelsman et al. | | 623/18.11 |
| 2003/0208276 A1 | 11/2003 | Berelsman et al. | | |
| 2003/0208277 A1 * | 11/2003 | Weiss et al. | | 623/20.12 |
| 2003/0232124 A1 | 12/2003 | Medlin et al. | | |
| 2004/0186581 A1 * | 9/2004 | Huene | | 623/20.12 |
| 2004/0220675 A1 * | 11/2004 | Lewis et al. | | 623/20.11 |
| 2004/0243243 A1 * | 12/2004 | Tornier | | 623/20.12 |
| 2005/0043806 A1 | 2/2005 | Cook et al. | | |
| 2006/0111788 A1 * | 5/2006 | Ball | | 623/20.11 |
| 2006/0173546 A1 * | 8/2006 | Berelsman et al. | | 623/20.11 |
| 2008/0033566 A1 * | 2/2008 | Berelsman et al. | | 623/20.12 |
| 2009/0024221 A1 * | 1/2009 | Ball | | 623/20.11 |
| 2009/0312840 A1 * | 12/2009 | Morrey | | 623/20.11 |
| 2010/0179661 A1 * | 7/2010 | Berelsman et al. | | 623/20.12 |

* cited by examiner

PROSTHETIC ELBOW REPLACEMENT

CROSS-REFERENCES TO RELATED APPLICATIONS

This application claims priority from U.S. Provisional Patent Application No. 60/816,947 filed Jun. 28, 2006.

STATEMENT REGARDING FEDERALLY SPONSORED RESEARCH

Not Applicable.

BACKGROUND OF THE INVENTION

1. Field of the Invention

The invention relates to a bone joint prosthesis, and more particularly to an elbow joint prosthesis used to replace a dysfunctional elbow joint.

2. Description of the Related Art

A variety of devices have been developed for elbow prosthetic reconstruction. Some commercially available prosthetic elbow replacement systems include: the Coonrad/Morrey Total Elbow available from Zimmer Inc., the Solar® total elbow system available from Stryker Orthopaedics, the Texx total elbow system available from Biotek, and the Discovery™ total elbow system available from Biomet. Various U.S. patents and U.S. patent applications also describe elbow joint prostheses, bone joint prostheses, and related instrumentation and procedures. See, for example, U.S. Pat. Nos. 2,696,817, 3,772,709, 3,816,854, 3,868,730, 3,939,496, 3,990,117, 4,008,495, 4,079,469, 4,131,956, 4,280,231, 4,293,963, 4,383,337, 4,538,306, 5,061,271, 5,314,484, 5,376,121, 5,723,015, 5,782,923, 5,954,770, 6,027,534, 6,290,725, 6,379,387, 6,699,290, 6,716,248, 6,767,368, 6,890,357, 6,997,957 and U.S. Patent Application Publication Nos. 2003/0208276, 2003/0232124 and 2005/0043806.

While these known prosthetic elbow replacement systems may be acceptable for certain applications, under certain circumstances some prosthetic elbow replacement systems have disadvantages. For instance, wear debris is one concern with respect to implant replacement of the elbow. This typically occurs if the humeral and ulnar stems are well fixed. The spectrum of pathology requires that a replacement is sometimes indicated in elbows with gross deformity. Thus, a stable implant that can tolerate the stresses at the stem bone interface and still provide some play at the articulation to lessen the likelihood of loosening is ideal. Yet wear of the articulation can occur under these circumstances.

Thus, there exists a need for an improved prosthetic elbow replacement system that addresses: (i) the instability of unlinked implants, (ii) the need for better wear characteristics than are now available in current linked implants, (iii) the need for a unique design of the ulnar component that lessens the possibility of malalignment, and (iv) the need for a design that allows the implant to be put in without cement should this be desired.

SUMMARY OF THE INVENTION

The present invention addresses the foregoing needs by providing a prosthetic elbow replacement system in which a hinge system is incorporated with the humeral component. In contrast to prior prosthetic elbow replacement systems, the hinged portion is enlarged and a central area is prepared in such a way as to receive the ulnar component. The hinge system includes a pivot pin with a throughhole that is tapered anteriorly and posteriorly. The pivot pin is mounted to the humeral component. Thus, the articulation is different from prior prosthetic elbow replacement systems. Specifically, the articulation may include an ulnar stem portion that is drawn into the throughhole in the pivot pin and secured with a fastener (e.g., a screw) and a posterior fitting element (e.g., an ulnar component mounting cap) which constitute other elements of the articulation. Flexion occurs with rotation of the pivot pin.

In one feature of the invention, the angular relationships of the humeral component and the ulnar component can be very carefully determined to allow about 7 to about 8 degrees of varus/valgus motion. This allows axial rotation of the ulna component in the humeral component as well. An additional important feature is that the articulation is metallic on metallic, thus lessening the likelihood of wear. Texturing of the humeral component and the ulnar component can be of tantalum (or trabecular metal). On the ulnar component, a plasma spray can be used, or the plasma spray can be replaced with tantalum.

In one aspect, the invention provides a prosthetic elbow replacement including a humeral component, a pivot pin, an ulnar component, and a fastener. The humeral component can have a humeral stem dimensioned to fit within a medullary canal of the humerus, and a yoke connected to the humeral stem. The yoke can terminate in a pair of spaced apart arms. The humeral stem can have a surface section of a porous material. The pivot pin can be disposed between the arms of the humeral component for rotational movement of the pivot pin with respect to the humeral component. The pivot pin can have a transverse throughhole having a first end opening and an opposite second end opening. The ulnar component can have an ulnar stem including a distal end dimensioned to fit within a medullary canal of the ulna and an opposite proximal end dimensioned to fit within the first end opening of the throughhole of the pivot pin. The ulnar stem can have a surface section of a porous material. The ulnar component can also have a mounting cap dimensioned to fit within the second end opening of the throughhole of the pivot pin. The fastener is for connecting the ulnar stem and the mounting cap such that the proximal end of the ulnar stem is positioned within the first end opening of the throughhole of the pivot pin and the mounting cap is positioned within the second end opening of the throughhole of the pivot pin.

In the prosthetic elbow replacement, an inner surface of the throughhole of the pivot pin can have an inside diameter that decreases from an outer surface of the pivot pin to an inner region of the pivot pin. The proximal end of the ulnar stem can taper inward toward an end surface of the proximal end of the ulnar stem, and an end of the mounting cap can taper inward toward an end surface of the mounting cap, and the end surface of the proximal end of the ulnar stem and the end surface of the mounting cap can be placed in contact when the fastener connects the ulnar stem and the mounting cap. The outer wall of the proximal end of the ulnar stem and an outer wall of the end of the mounting cap can be spaced from the inner surface of the throughhole of the pivot pin when the fastener connects the ulnar stem and the mounting cap. In one form, the inner surface of the throughhole of the pivot pin has a generally hourglass shape, and the outer wall of the proximal end of the ulnar stem and the outer wall of the end of the mounting cap together have a generally hourglass shape when the fastener connects the ulnar stem and the mounting cap.

The humeral component can include a flange that is spaced from the humeral stem and that extends away from the yoke. The flange can have a curved end integral with the humeral stem and an elongated stem substantially parallel with the humeral stem. The flange can also have a surface section of a porous material. The mounting cap can have a dome shaped top surface, and an inner surface of the yoke of the humeral component can be concave such that the dome shaped top surface of the mounting cap is spaced from the yoke. Each of the arms of the humeral component can include an outwardly facing recess, and the pivot pin can include a first end that rotates in one of the recesses and a second end that rotates in the other recess.

The proximal end of the ulnar stem, and the mounting cap, and the throughhole of the pivot pin can each be dimensioned to allow for varus/valgus motion of the ulnar component when the fastener connects the ulnar stem and the mounting cap. Preferably, the proximal end of the ulnar stem, and the mounting cap, and the throughhole of the pivot pin are each dimensioned to allow for about 7 to about 8 degrees of varus/valgus motion of the ulnar component. In one form, surfaces of the humeral component that contact the pivot pin consist essentially of metallic material, surfaces of the pivot pin that contact the ulnar component consist essentially of metallic material, surfaces of the ulnar component that contact the pivot pin consist essentially of metallic material, and surfaces of the mounting cap that contact the pivot pin consist essentially of metallic material. As a result, the articulation will be metallic on metallic, thus lessening the likelihood of wear.

In another aspect, the invention provides a prosthetic joint replacement including a first component, a pivot pin, a second component, and a fastener. The first component can have a first stem dimensioned to fit within a medullary canal of a first bone and a yoke connected to the first stem. The yoke can terminate in a pair of spaced apart arms. The first stem can have a surface section of a porous material. The pivot pin can be disposed between the arms of the first component for rotational movement of the pivot pin with respect to the first component. The pivot pin can have a transverse throughhole having a first end opening and an opposite second end opening. The second component can have a second stem including a distal end dimensioned to fit within a medullary canal of a second bone and an opposite proximal end dimensioned to fit within the first end opening of the throughhole of the pivot pin. The second stem can have a surface section of a porous material. The second component can also have a mounting cap dimensioned to fit within the second end opening of the throughhole of the pivot pin. The fastener is for connecting the second stem and the mounting cap such that the proximal end of the second stem is positioned within the first end opening of the throughhole of the pivot pin and the mounting cap is positioned within the second end opening of the throughhole of the pivot pin.

In the prosthetic joint replacement, an inner surface of the throughhole of the pivot pin can have an inside diameter that decreases from an outer surface of the pivot pin to an inner region of the pivot pin. The proximal end of the second stem can taper inward toward an end surface of the proximal end of the second stem, and an end of the mounting cap can taper inward toward an end surface of the mounting cap, and the end surface of the proximal end of the second stem and the end surface of the mounting cap can be placed in contact when the fastener connects the second stem and the mounting cap. The outer wall of the proximal end of the second stem and an outer wall of the end of the mounting cap can be spaced from the inner surface of the throughhole of the pivot pin when the fastener connects the second stem and the mounting cap. In one form, the inner surface of the throughhole of the pivot pin has a generally hourglass shape, and the outer wall of the proximal end of the second stem and the outer wall of the end of the mounting cap together have a generally hourglass shape when the fastener connects the second stem and the mounting cap.

The first component can include a flange that is spaced from the first stem and that extends away from the yoke. The flange can have a curved end integral with the first stem and an elongated stem substantially parallel with the first stem. The mounting cap can have a dome shaped top surface, and an inner surface of the yoke of the first component can be concave such that the dome shaped top surface of the mounting cap is spaced from the yoke. Each of the arms of the first component can include an outwardly facing recess, and the pivot pin can include a first end that rotates in one of the recesses and a second end that rotates in the other recess.

The proximal end of the second stem, and the mounting cap, and the throughhole of the pivot pin can each be dimensioned to allow for varus/valgus motion of the second component when the fastener connects the second stem and the mounting cap. Preferably, the proximal end of the second stem, and the mounting cap, and the throughhole of the pivot pin are each dimensioned to allow for about 7 to about 8 degrees of varus/valgus motion of the second component. In one form, surfaces of the first component that contact the pivot pin consist essentially of metallic material, surfaces of the pivot pin that contact the second component consist essentially of metallic material, surfaces of the second component that contact the pivot pin consist essentially of metallic material, and surfaces of the mounting cap that contact the pivot pin consist essentially of metallic material. As a result, the articulation will be metallic on metallic, thus lessening the likelihood of wear.

In yet another aspect, the invention provides a kit for assembly into a prosthetic elbow replacement. The kit includes a humeral component, a pivot pin, an ulnar component, a mounting cap, and a fastener. The humeral component can have a humeral stem dimensioned to fit within a medullary canal of the humerus and a yoke connected to the humeral stem. The yoke can terminate in a pair of spaced apart arms. The humeral stem can have a surface section of a porous material. The pivot pin can be dimensioned to be disposed between the arms of the humeral component for rotational movement of the pivot pin with respect to the humeral component. The pivot pin has an axis of rotation, and a throughhole having a first end opening and an opposite second end opening. The throughhole of the pivot pin can be transverse to the axis of rotation of the pivot pin. The ulnar component can have an ulnar stem including a distal end dimensioned to fit within a medullary canal of the ulna and an opposite proximal end dimensioned to fit within the first end opening of the throughhole of the pivot pin. The ulnar stem can have a surface section of a porous material. The mounting cap can have an end section dimensioned to fit within the second end opening of the throughhole of the pivot pin. The fastener is suitable for connecting the ulnar stem and the mounting cap within the throughhole of the pivot pin.

In one form, the inner surface of the throughhole of the pivot pin can have an inside diameter that decreases from an outer surface of the pivot pin to an inner region of the pivot pin. The proximal end of the ulnar stem can taper inward toward an end surface of the proximal end of the ulnar stem, and the end section of the mounting cap can taper inward toward an end surface of the mounting cap. The end surface of the proximal end of the ulnar stem and the end surface of the mounting cap can be dimensioned to be placed in mating contact when the fastener connects the ulnar stem and the mounting cap. An outer wall of the proximal end of the ulnar stem and an outer wall of the end section of the mounting cap can be dimensioned to be spaced from an inner surface of the throughhole of the pivot pin when the fastener connects the ulnar stem and the mounting cap. In one embodiment, an inner surface of the throughhole of the pivot pin has a generally hourglass shape, and the outer wall of the proximal end of the ulnar stem and the outer wall of the end section of the mounting cap together have a generally hourglass shape when the fastener connects the ulnar stem and the mounting cap.

The humeral component can include a flange that is spaced from the humeral stem and that extends away from the yoke. The flange can have a curved end integral with the humeral stem and an elongated stem substantially parallel with the humeral stem. The mounting cap can have a dome shaped top surface, and an inner surface of the yoke of the humeral component can be concave such that the dome shaped top surface of the mounting cap is spaced from the yoke.

Each of the arms of the humeral component can include an outwardly facing recess, and the pivot pin can include a first end dimensioned to rotate in one of the recesses and a second end dimensioned to rotate in the other recess. The pivot pin can include a body having a cylindrical central section and having an end flange extending radially outward from a first end of the body, a disk, and a pin fastener for fastening the disk to an opposite second end of the body. The end flange can rotate in one of the recesses of the arms of the humeral component and the disk can rotate in the other recess.

In one form, surfaces of the humeral component that contact the pivot pin consist essentially of metallic material, surfaces of the pivot pin that contact the ulnar component consist essentially of metallic material, surfaces of the ulnar component that contact the pivot pin consist essentially of metallic material, and surfaces of the mounting cap that contact the pivot pin consist essentially of metallic material. In another form, the humeral component consists essentially of metallic material, the pivot pin consists essentially of metallic material, and the ulnar component consists essentially of metallic material. As a result, the articulation in the assembled prosthetic elbow replacement will be metallic on metallic, thus lessening the likelihood of wear.

In still another aspect, the invention provides a kit for assembly into a prosthetic joint replacement. The kit can include a first component, a pivot pin, a second component, a mounting cap, and a fastener. The first component can have a first stem dimensioned to fit within a medullary canal of a first bone and a yoke connected to the first stem. The yoke can terminate in a pair of spaced apart arms. The first stem can have a surface section of a porous material. The pivot pin can be dimensioned to be disposed between the arms of the first component for rotational movement of the pivot pin with respect to the first component. The pivot pin has an axis of rotation, and a throughhole having a first end opening and an opposite second end opening. The throughhole can be transverse to the axis of rotation of the pivot pin. The second component can have a second stem including a distal end dimensioned to fit within a medullary canal of a second bone and an opposite proximal end dimensioned to fit within the first end opening of the throughhole of the pivot pin. The second stem can have a surface section of a porous material. The mounting cap can have an end section dimensioned to fit within the second end opening of the throughhole of the pivot pin. The fastener is suitable for connecting the second stem and the mounting cap within the throughhole of the pivot pin.

In one form, the inner surface of the throughhole of the pivot pin can have an inside diameter that decreases from an outer surface of the pivot pin to an inner region of the pivot pin. The proximal end of the second stem can taper inward toward an end surface of the proximal end of the second stem, and the end section of the mounting cap can taper inward toward an end surface of the mounting cap. The end surface of the proximal end of the second stem and the end surface of the mounting cap can be dimensioned to be placed in mating contact when the fastener connects the second stem and the mounting cap. An outer wall of the proximal end of the second stem and an outer wall of the end section of the mounting cap can be dimensioned to be spaced from an inner surface of the throughhole of the pivot pin when the fastener connects the second stem and the mounting cap. In one embodiment, an inner surface of the throughhole of the pivot pin has a generally hourglass shape, and the outer wall of the proximal end of the second stem and the outer wall of the end section of the mounting cap together have a generally hourglass shape when the fastener connects the second stem and the mounting cap.

The first component can include a flange that is spaced from the first stem and that extends away from the yoke. The flange can have a curved end integral with the first stem and an elongated stem substantially parallel with the first stem. The mounting cap can have a dome shaped top surface, and an inner surface of the yoke of the first component can be concave such that the dome shaped top surface of the mounting cap is spaced from the yoke.

Each of the arms of the first component can include an outwardly facing recess, and the pivot pin can include a first end dimensioned to rotate in one of the recesses and a second end dimensioned to rotate in the other recess. The pivot pin can include a body having a cylindrical central section and having an end flange extending radially outward from a first end of the body, a disk, and a pin fastener for fastening the disk to an opposite second end of the body. The end flange can rotate in one of the recesses of the arms of the first component and the disk can rotate in the other recess.

In one form, surfaces of the first component that contact the pivot pin consist essentially of metallic material, surfaces of the pivot pin that contact the second component consist essentially of metallic material, surfaces of the second component that contact the pivot pin consist essentially of metallic material, and surfaces of the mounting cap that contact the pivot pin consist essentially of metallic material. In another form, the first component consists essentially of metallic material, the pivot pin consists essentially of metallic material, and the second component consists essentially of metallic material. As a result, the articulation in the assembled prosthetic joint replacement will be metallic on metallic, thus lessening the likelihood of wear.

It is therefore an advantage of the invention to provide a prosthetic elbow replacement system that includes improved ulnar articulation.

It is another advantage of the invention to provide a prosthetic elbow replacement system that includes a rotating pin arrangement such that flexion occurs with rotation of the pivot pin and controlled varus/valgus motion is possible.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DESCRIPTION OF THE INVENTION

Figures 1, 1A:
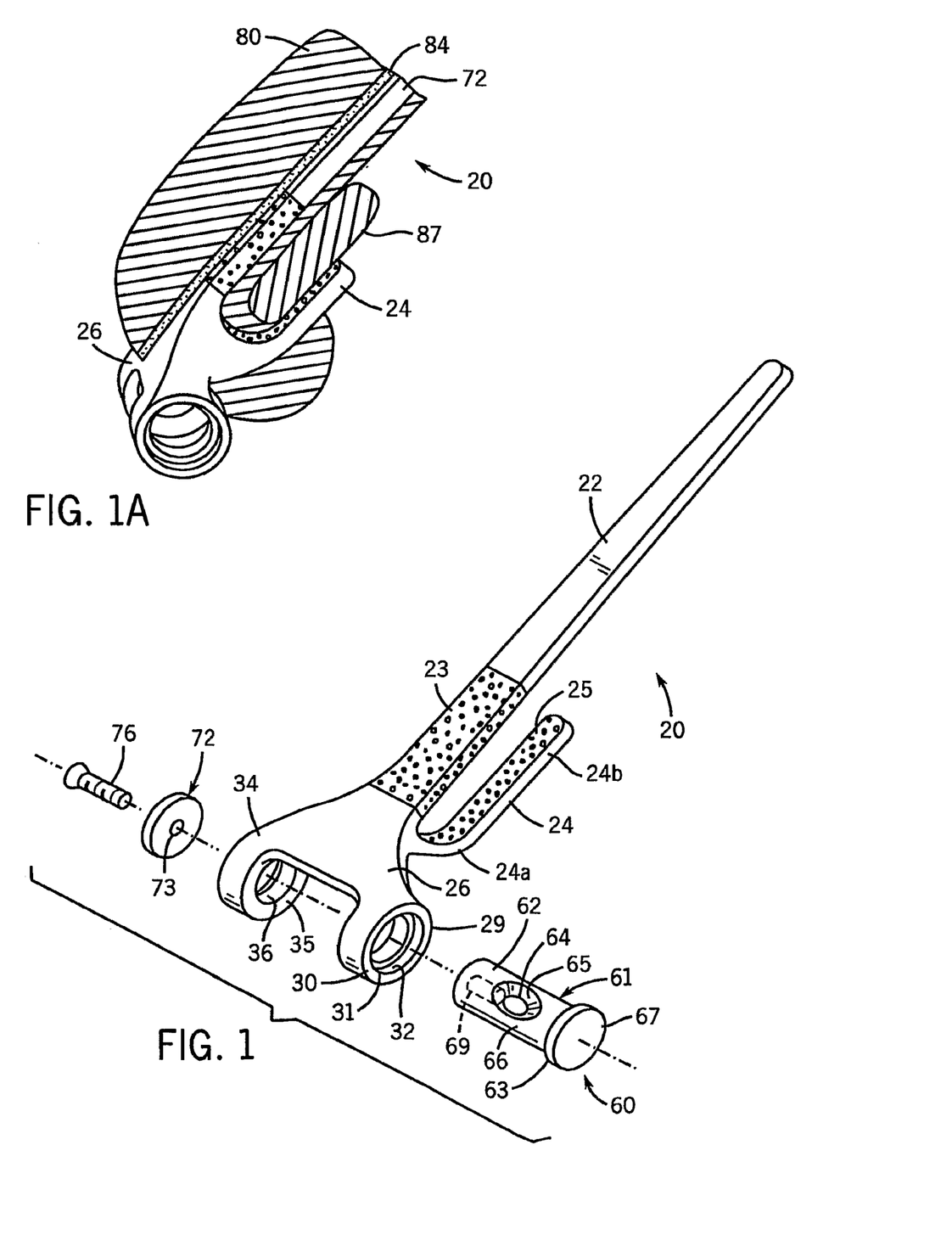
FIG. 1 is an exploded perspective view of the humeral component of a prosthetic elbow replacement according to the invention.
FIG. 1A shows the stem of the humeral component of the prosthetic elbow replacement of FIG. 1 inserted in a humerus.
Figures 4, 5, 6:
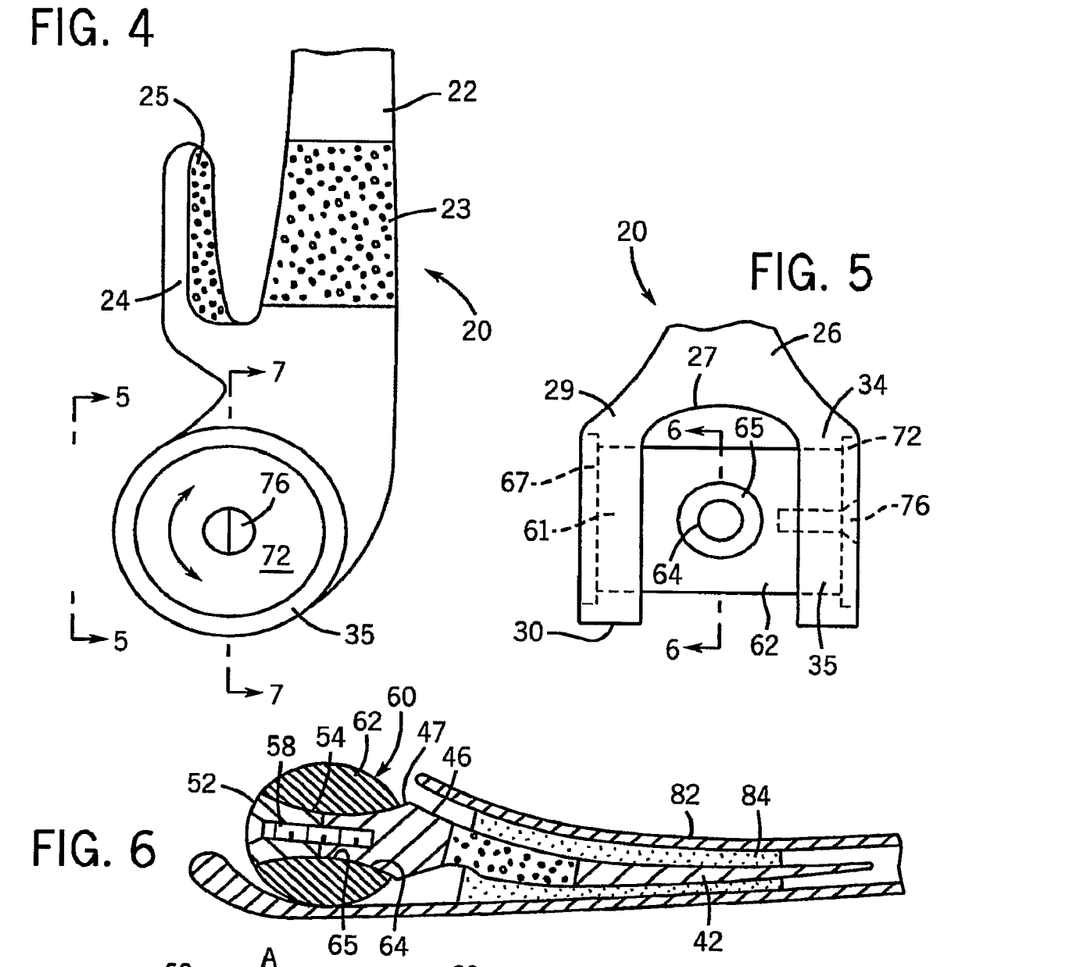
FIG. 4 is a side view of the humeral component of FIG. 1 with the rotating pivot pin assembled in the humeral component.
FIG. 5 is a partial view of the humeral component and pivot pin taken along line 5-5 of FIG. 4.
FIG. 6 is a view taken along line 6-6 of FIG. 5 showing a lateral view of the ulnar component and the rotating pivot pin in an assembled state, the ulnar stem being inserted in the medullary canal of the ulna.

Looking first at FIGS. 1 and 5, there is shown a humeral component 20 of a prosthetic elbow replacement according to the invention. The humeral component 20 may be formed from: (i) a metal or metal alloy such as a titanium alloy (e.g., titanium-6-aluminum-4-vanadium), a cobalt alloy, a stainless steel alloy, or tantalum; (ii) a nonresorbable ceramic such as aluminum oxide or zirconia; (iii) a nonresorbable polymeric material such as polyethylene; or (iv) a nonresorbable composite material such as a carbon fiber-reinforced polymers (e.g., polysulfone). Preferably, the humeral component 20 is formed from a metal alloy, and most preferably, the humeral component 20 is formed from a cobalt chrome alloy.

The humeral component 20 has an elongated stem portion 22 with a porous surface section 23 into which bone tissue can grow and/or bone cement can infiltrate. The humeral component 20 also has a J-shaped flange 24 with a porous surface section 25 into which bone tissue can grow and/or bone cement can infiltrate. The flange 24 includes a curved end 24a integral with the humeral stem portion 22 and an elongated stem 24b spaced from and substantially parallel with the humeral stem portion 22. Various stem and flange dimensions are possible, including without limitation, 4" small, 6" small, 8" small, 4" regular, 6" regular, 8" regular, 4" x-small, 6" x-small, 6" small with long flange, 8" small with long flange, 6" regular with long flange, and 8" regular with long flange.

The porous surface sections 23, 25 of the humeral component 20 can be formed using various techniques such as plasma spraying of a metal powder, sintering of metal beads, or diffusion bonding of metal wire mesh. In one form, the porous surface sections 23, 25 comprise a porous material, and preferably comprise a porous metallic material having a network of interconnected pores distributed throughout the metallic material chosen to ensure that the resulting interstitial pore size is at least sufficient to permit bone tissue to grow into the porous material. Preferably, the metallic particles are formed from titanium, titanium alloys, cobalt alloys, stainless steel alloys, tantalum, and mixtures thereof, and most preferably, the metallic particles are formed from tantalum. Various methods are known for forming the porous material on the stem 22 and flange 24, such as the methods described in U.S. Pat. Nos. 5,734,959, 4,206,516 and 3,855,638 and U.S. Patent Application Publication No. 2003/0232124, which are incorporated herein by reference along with all other documents cited herein. The porous surface sections 23, 25 may also include a textured surface comprising a plurality of depressions such as grooves, dimples, or the like. Further, the porous surface sections 23, 25 may also have a coating of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof.

The humeral component 20 also has a yoke section 26 with a curved concave inner surface 27 (see FIG. 5). One side of the yoke section 26 has an arm 29 that terminates in a circular section 30 having a central hole 31. The circular section 30 has an annular end section recess 32 of increased inside diameter in relation to the central hole 31 that allows for rotation of a section of a pivot pin as described below. Another side of the yoke section 26 has an arm 34 that terminates in a circular section 35 having a central hole 36. The circular section 35 has an annular end section recess 37 of increased inside diameter in relation to the central hole 36 (identical to end section recess 32, see FIG. 7) that allows for rotation of a section of a pivot pin as described below.

Figure 2:
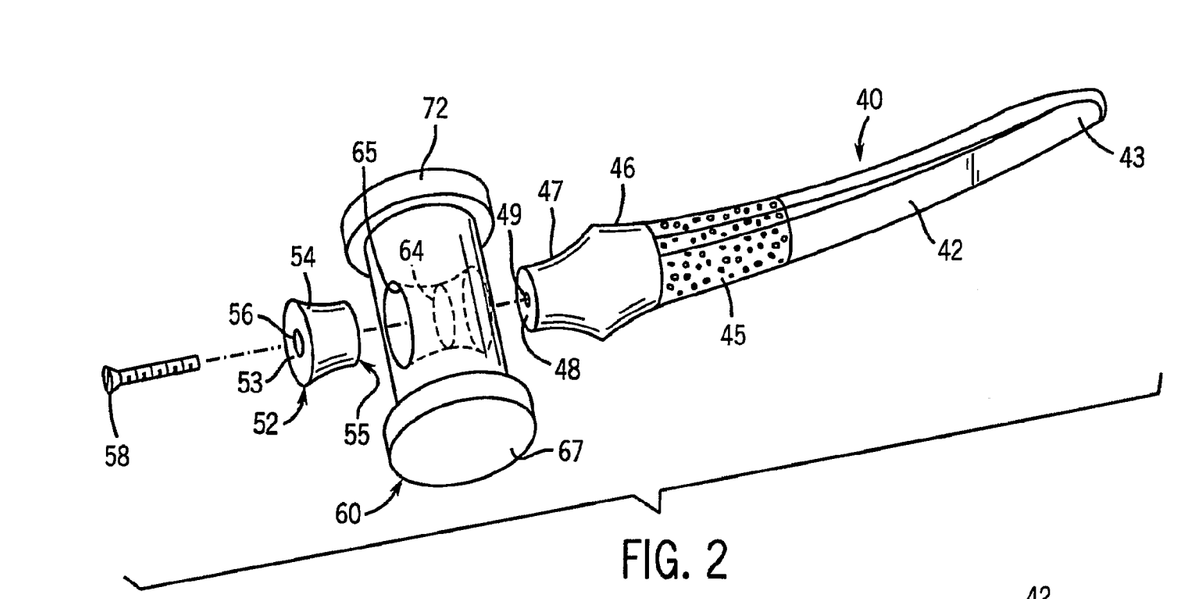
FIG. 2 is an exploded perspective view of the ulnar component and the rotating pivot pin of a prosthetic elbow replacement according to the invention.
Figure 3:
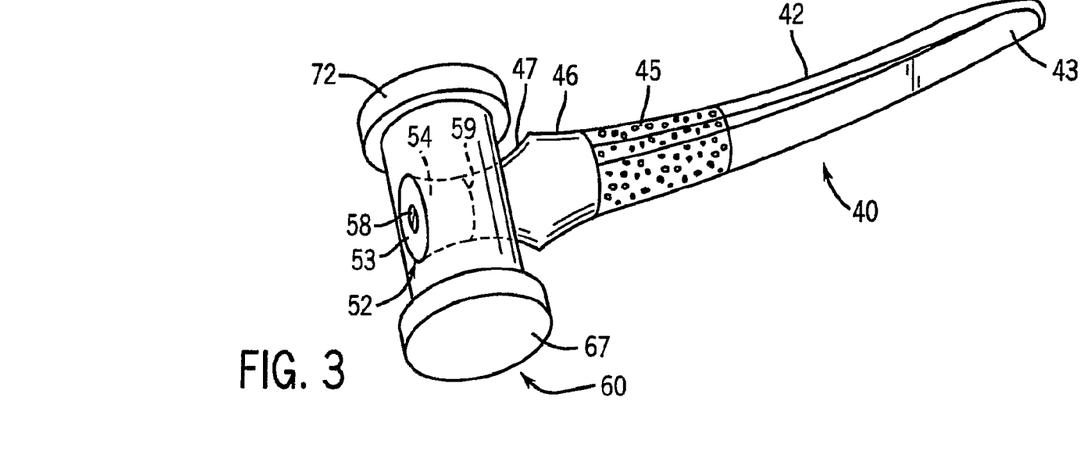
FIG. 3 is a perspective view of the ulnar component and the rotating pivot pin of FIG. 2 in an assembled state.

Looking now at FIGS. 2 and 3, there is shown a stem 42 of an ulnar component 40 of a prosthetic elbow replacement according to the invention. The stem 42 of the ulnar component 40 may be formed from: (i) a metal or metal alloy such as a titanium alloy (e.g., titanium-6-aluminum-4-vanadium), a cobalt alloy, a stainless steel alloy, or tantalum; (ii) a nonresorbable ceramic such as aluminum oxide or zirconia; (iii) a nonresorbable polymeric material such as polyethylene; or (iv) a nonresorbable composite material such as a carbon fiber-reinforced polymers (e.g., polysulfone). Preferably, the stem 42 of the ulnar component 40 is formed from a metal alloy, and most preferably, the stem 42 is formed from a cobalt chrome alloy.

The stem 42 of the ulnar component 40 has a distal end 43 that is inserted in the medullary canal of the ulna. The stem 42 of the ulnar component 40 has a porous surface section 45 into which bone tissue can grow and/or bone cement can infiltrate. Various stem dimensions are suitable for the stem 42 of the ulnar component 40 including without limitation, small left, small right, regular left, regular right, long small left, long small right, long regular left, long regular right, x-long x-small left, x-long x-small right.

The porous surface section 45 of the stem 42 of the ulnar component 40 can be formed using various techniques such as plasma spraying of a metal powder, sintering of metal beads, or diffusion bonding of metal wire mesh. In one form, the porous surface section 45 comprises a porous material, and preferably comprises a porous metallic material having a network of interconnected pores distributed throughout the metallic material chosen to ensure that the resulting interstitial pore size is at least sufficient to permit bone tissue to grow into the porous material. Preferably, the metallic particles are formed from titanium, titanium alloys, cobalt alloys, stainless steel alloys, tantalum, and mixtures thereof, and most preferably, the metallic particles are formed from tantalum. The porous surface section 45 may also include a textured surface comprising a plurality of depressions such as grooves, dimples, or the like. Further, the porous surface section 45 may also have a coating of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof.

On the side of the porous surface section 45 opposite the distal end 43 of the stem 42, the outer surface of the stem 42 of the ulnar component 40 has an outwardly curved section 46 that merges with an inwardly curved section 47 that terminates in a proximal end surface 48 of the stem 42 of the ulnar component 40. An internally threaded inwardly directed axial hole 49 is centrally located in the end surface 48 of the stem 42 of the ulnar component 40.

The ulnar component 40 also includes a mounting cap 52 having a dome shaped top surface 53 and a side wall 54 that tapers inwardly from the top surface 53. The side wall 54 terminates in an end surface 55 of the cap 52 of the ulnar component 40. An internally threaded throughhole 56 extends from the top surface 53 to the end surface 55 of the cap 52. The ulnar component 40 also includes a screw 58 that engages the threads of the throughhole 56 of the cap 52 and engages the threads of the axial hole 49 of the stem 42 when the cap 52 is assembled to the stem 42 as shown in FIG. 3, thereby creating an interface 59 between the end surface 55 of the cap 52 and the end surface 48 of the stem 42.

Looking at FIGS. 1 to 7, there is shown a pivot pin 60 of a prosthetic elbow replacement according to the invention. The pivot pin 60 may be formed from: (i) a metal or metal alloy such as a titanium alloy (e.g., titanium-6-aluminum-4-vanadium), a cobalt alloy, a stainless steel alloy, or tantalum; (ii) a nonresorbable ceramic such as aluminum oxide or zirconia; (iii) a nonresorbable polymeric material such as polyethylene; or (iv) a nonresorbable composite material such as a carbon fiber-reinforced polymers (e.g., polysulfone). Preferably, the pivot pin 60 is formed from a metal alloy, and most preferably, the pivot pin 60 is formed from a cobalt chrome alloy.

Figure 7:
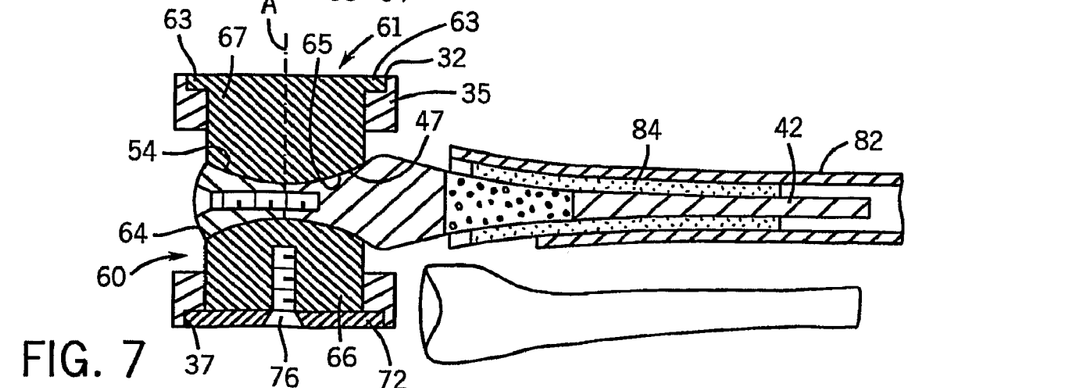
FIG. 7 is a view taken along line 7-7 of FIG. 4 showing a top view of the ulnar component and the rotating pivot pin in an assembled state, the ulnar stem being inserted in the medullary canal of the ulna.

As shown in FIGS. 1 and 7, the pivot pin 60 includes a main body 61 having a cylindrical central section 62 and having a disk shaped end section 67 that defines an end flange 63. The cylindrical central section 62 has a transverse throughhole 64 with an inner surface 65 having a generally hourglass shape (see FIG. 7). In one example form, the inner surface 65 of the throughhole 64 has an inside diameter that continuously decreases from the outer surface 66 of the cylindrical central section 62 to the central axis of rotation A of the cylindrical central section 62 of the pivot pin 60 (see FIG. 7). The cylindrical central section 62 also has an internally threaded inwardly directed axial hole 69 centrally located in the end of the cylindrical central section 62 opposite the end section 67.

The pivot pin 60 also includes a removable disk 72 having a central throughhole 73. The pivot pin 60 further includes a pin fastener, screw 76, that engages the inner surface of the throughhole 73 of the disk 72 and engages the threads of the axial hole 69 of the cylindrical central section 62 of the pivot pin 60 when the disk 72 is assembled to the cylindrical central section 62 as shown in FIG. 7. When the pivot pin 60 is assembled to the humeral component 20 as shown in FIG. 7, the disk 72 can rotate in the end section recess 37 of the circular section 35 of the humeral component 20 and the end flange 63 can rotate in the end section recess 32 of the circular section 30 of the humeral component 20. The cylindrical central section 62 of the pivot pin 60 rotates in the other sections of the central holes 31, 36. It should be appreciated that other means for installing the pivot pin on the humeral component 20 are contemplated and that the construction of the pivot pin 60 described herein is one example of a means for installing the pivot pin on the humeral component 20.

The surface of the disk 72, the surface of the end section recess 37, the surface of the end flange 63, the surface of the end section recess 32, the surface of the cylindrical central section 62 of the pivot pin 60, and the surfaces of the central holes 31, 36 are preferably metallic such that the articulation will be metallic on metallic, thus lessening the likelihood of wear. In one form, the humeral component consists essentially of metallic material, the pivot pin consists essentially of metallic material, and the ulnar component consists essentially of metallic material such that the articulation will be metallic on metallic, thus lessening the likelihood of wear.

Referring to FIGS. 1A, 6 and 7, the prosthetic elbow replacement may be inserted in a patient as follows. First, the mid-portion of the trochlea is removed to facilitate access to the medullary canal of the humerus 80. The medullary canal of the humerus is then reamed, and a cutting guide is used to provide for accurate removal of the articular surface of the distal humerus. Next, the medullary canal of the ulna 82 is located and then reamed. Cement 84 is then injected down the medullary canal of both the ulna and humerus. Of course, the surgeon may decide to rely on a "press-fit" (sometimes called an "interference fit") for implantation of the humeral component 20 in the humerus 80 and the ulnar component 40 in the ulna 82 such that the bone cement 84 can be omitted.

The ulnar stem 42 of the ulnar component 40 is then inserted in the medullary canal of the ulna 82. A T-shaped instrument having an elongated shaft with an externally threaded distal end (such as that described in U.S. Pat. No. 5,061,271) can be useful for inserting the ulnar stem 42 in the medullary canal of the ulna 82. For instance, the externally threaded distal end of the instrument can be threaded into the internally threaded axial hole 49 of the ulnar stem 42 for positioning the ulnar stem 42 in the medullary canal of the ulna 82. After positioning the ulnar stem 42 in the medullary canal of the ulna 82, the externally threaded distal end of the T-shaped instrument can be removed from the internally threaded axial hole 49 of the ulnar stem 42. The T-shaped instrument can insert the ulnar stem 42 to the proper depth and rotation. Extraction of the ulnar stem 42 from the medullary canal of the ulna 82 can also be accomplished using the T-shaped instrument. An alternative for extraction is a vise-grip that grabs the dimples of the proximal ulna as it is exposed in the area of the olecranon articulation.

Next, a bone graft 87 is prepared. The stem 22 of the humeral component 20 is inserted down the medullary canal of the humerus 80 and the bone graft 87 is positioned to be captured by the flange 24 of the humeral component 20 as shown in FIG. 1A. A humeral impactor can be used to insert the humerus to its optimum position prior to the articulation with the ulna.

The assembly of the rotating pivot pin 60 to the humeral component 20 can be done at the time of implantation on the back table. The pivot pin 60 is also able to be disassembled for the purpose of applying a resurfacing implant and then can in turn be easily converted to the linked implant.

After the humeral component 20 and the ulnar component 40 are inserted in the humerus and ulna, the inwardly curved section 47 of the ulnar stem 42 of the ulnar component 40 is inserted into one end of the throughhole 64 of the cylindrical central section 62 of the pivot pin 60. The T-shaped instrument shaft can be inserted through the throughhole 64 of the cylindrical central section 62 of the pivot pin 60 and used to capture the stem 42 of the ulnar component 40 and pull the stem 42 into the throughhole 64 of the cylindrical central section 62 of the pivot pin 60. The outer side wall 54 of the cap 52 of the ulnar component 40 is then inserted into the opposite end of the throughhole 64 of the cylindrical central section 62 of the pivot pin 60. The screw 58 is then screwed into the throughhole 56 of the cap 52 so that the screw 58 engages the threads of the throughhole 56 of the cap 52 and engages the threads of the axial hole 49 of the stem 42 such that the cap 52 is assembled to the stem 42 as shown in FIGS. 3 and 7.

When the prosthetic elbow replacement is inserted in a patient, flexion occurs by rotation of the disk 72 of the pivot pin 60 in the end section recess 37 of the central hole 36 of the circular section 35 of the humeral component 20 and by rotation of the end flange 63 of the pivot pin in the end section recess 32 of the central hole 31 of the circular section 30 of the humeral component 20 and by rotation of the cylindrical central section 62 of the pivot pin 60 in the other sections of the central holes 31, 36. Of course, different means for installing the pivot pin in the humeral component 20 will provide for different means for rotation of the pivot pin with respect to the humeral component 20.

Varus/valgus motion is provided by movement of the inwardly curved section 47 of the end surface 48 of the stem 42 of the ulnar component 40 and by movement of the outer side wall 54 of the cap 52 of the ulnar component 40 within the hourglass-shaped inner surface 65 of the throughhole 64 of the pivot pin 60. The curved inner surface 27 of the yoke section 26 also provides space for varus valgus movement of the cap 52 of the ulnar component 40.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

INDUSTRIAL APPLICABILITY

The invention provides a prosthetic elbow replacement for a dysfunctional elbow joint.

What is claimed is:

1. A prosthetic joint replacement comprising:
a first component having a first stem dimensioned to fit within a medullary canal of a first bone and having a yoke connected to the first stem, the yoke terminating in a pair of spaced apart arms;
a pivot pin mounted between the arms of the first component for rotational movement with respect to the first component, the pivot pin having a transverse throughhole having a first end opening and an opposite second end opening, the pivot pin having an axis of rotation wherein the axis of rotation of the pivot pin intersects an inner surface of the throughhole;
a second component having a second stem including a distal end dimensioned to fit within a medullary canal of a second bone and an opposite proximal end dimensioned to fit within the first end opening of the throughhole of the pivot pin, the second component also having a mounting cap dimensioned to fit within the second end opening of the throughhole of the pivot pin; and
a fastener for connecting the second stem and the mounting cap,
wherein the fastener connects the second stem and the mounting cap such that the proximal end of the second stem is positioned within the first end opening of the throughhole of the pivot pin and the mounting cap is positioned within the second end opening of the throughhole of the pivot pin.

2. The prosthetic joint replacement of claim 1 wherein:
the inner surface of the throughhole of the pivot pin has an inside diameter that decreases from an outer surface of the pivot pin to an inner region of the pivot pin.

3. The prosthetic joint replacement of claim 2 wherein:
the proximal end of the second stem tapers inward toward an end surface of the proximal end of the second stem, and an end of the mounting cap tapers inward toward an end surface of the mounting cap, and
the end surface of the proximal end of the second stem and the end surface of the mounting cap are placed in contact when the fastener connects the second stem and the mounting cap.

4. The prosthetic joint replacement of claim 3 wherein:
an outer wall of the proximal end of the second stem and an outer wall of the end of the mounting cap are spaced from the inner surface of the throughhole of the pivot pin when the fastener connects the second stem and the mounting cap.

5. The prosthetic joint replacement of claim 4 wherein:
the inner surface of the throughhole of the pivot pin has a generally hourglass shape, and
the outer wall of the proximal end of the second stem and the outer wall of the end of the mounting cap together have a generally hourglass shape when the fastener connects the second stem and the mounting cap.

6. The prosthetic joint replacement of claim 5 wherein:
the mounting cap has a dome shaped top surface.

7. The prosthetic joint replacement of claim 6 wherein:
an inner surface of the yoke of the first component is concave such that the dome shaped top surface of the mounting cap is spaced from the yoke.

8. The prosthetic joint replacement of claim 1 wherein:
the proximal end of the second stem, and the mounting cap, and the throughhole of the pivot pin are dimensioned to allow for varus/valgus motion of the second component when the fastener connects the second stem and the mounting cap.

9. The prosthetic joint replacement of claim 1 wherein:
an outer wall of the proximal end of the second stem and an outer wall of the end of the mounting cap are spaced from the inner surface of the throughhole of the pivot pin when the fastener connects the second stem and the mounting cap.

10. The prosthetic joint replacement of claim 1 wherein:
the first bone is the humerus, and
the second bone is the ulna.

11. A kit for assembly into a prosthetic joint replacement, the kit comprising:
a first component having a first stem dimensioned to fit within a medullary canal of a first bone and having a yoke connected to the first stem, the yoke terminating in a pair of spaced apart arms;
a pivot pin dimensioned to be disposed between the arms of the first component for rotational movement of the pivot pin with respect to the first component, the pivot pin having an axis of rotation, the pivot pin having a throughhole having a first end opening and an opposite second end opening, the throughhole being transverse to the axis of rotation of the pivot pin, wherein the axis of rotation of the pivot pin intersects an inner surface of the throughhole;
a second component having a second stem including a distal end dimensioned to fit within a medullary canal of a second bone and an opposite proximal end dimensioned to fit within the first end opening of the throughhole of the pivot pin;
a mounting cap having an end section dimensioned to fit within the second end opening of the throughhole of the pivot pin; and
a fastener for connecting the second stem and the mounting cap within the throughhole of the pivot pin.

12. The kit of claim 11 wherein:
the inner surface of the throughhole of the pivot pin has an inside diameter that decreases from an outer surface of the pivot pin to an inner region of the pivot pin.

13. The kit of claim 11 wherein:
the first component includes a flange that is spaced from the first stem, the flange extending away from the yoke.

14. The kit of claim 11 wherein:
the proximal end of the second stem tapers inward toward an end surface of the proximal end of the second stem, and
the end section of the mounting cap tapers inward toward an end surface of the mounting cap, and
the end surface of the proximal end of the second stem and the end surface of the mounting cap are dimensioned to be placed in mating contact when the fastener connects the second stem and the mounting cap.

15. The kit of claim 11 wherein:
an outer wall of the proximal end of the second stem and an outer wall of the end section of the mounting cap are dimensioned to be spaced from the inner surface of the throughhole of the pivot pin when the fastener connects the second stem and the mounting cap.

16. The kit of claim 11 wherein:
the inner surface of the throughhole of the pivot pin has a generally hourglass shape, and
the outer wall of the proximal end of the second stem and the outer wall of the end section of the mounting cap together have a generally hourglass shape when the fastener connects the second stem and the mounting cap.

17. The kit of claim 11 wherein:
the mounting cap has a dome shaped top surface opposite the end surface of the mounting cap.

18. The kit of claim 11 wherein:
an inner surface of the yoke of the first component has a concave section.

19. The kit of claim 11 wherein the pivot pin comprises:
a body having a cylindrical central section and having an end flange extending radially outward from a first end of the body;
a disk; and
a pin fastener for fastening the disk to an opposite second end of the body.

20. The kit of claim 11 wherein:
the first bone is the humerus, and
the second bone is the ulna.

* * * * *